United States Patent [19]

Blacklock

[11] Patent Number: 5,601,429
[45] Date of Patent: Feb. 11, 1997

[54] DENTAL IMPLANT ANCHOR

[76] Inventor: Gordon D. Blacklock, 14116 Grand NE., Albuquerque, N.M. 87123

[21] Appl. No.: 514,386
[22] Filed: Aug. 11, 1995
[51] Int. Cl.$^6$ ........................................... A61C 8/00
[52] U.S. Cl. ........................ 433/174; 433/172; 433/173; 433/175; 433/176
[58] Field of Search ................................... 433/172, 173, 433/174, 175, 176

[56] References Cited

U.S. PATENT DOCUMENTS

| | | | |
|---|---|---|---|
| 4,531,915 | 7/1985 | Tatum, Jr. | 433/176 |
| 4,826,434 | 5/1989 | Krueger | 433/174 |
| 4,863,383 | 9/1989 | Grafelmann | 433/174 |
| 5,000,686 | 3/1991 | Lazzara et al. | 433/174 |
| 5,074,790 | 12/1991 | Bauer | 433/174 |
| 5,078,607 | 1/1992 | Niznick | 433/174 |
| 5,194,000 | 3/1993 | Dury | 433/173 |
| 5,246,369 | 9/1993 | Poulmaire | 433/173 |
| 5,312,256 | 5/1994 | Scortecci | 433/174 |
| 5,376,004 | 12/1994 | Mena . | |
| 5,427,527 | 6/1995 | Niznick et al. | 433/174 |
| 5,468,149 | 11/1995 | D'Alise | 433/173 |
| 5,489,210 | 2/1996 | Hanosh | 433/173 |

Primary Examiner—Nicholas D. Lucchesi
Assistant Examiner—Jinan Glasgow
Attorney, Agent, or Firm—Terrance L. Siemens

[57] ABSTRACT

An anchor for a dental implant, having a compact cavity for receiving the post of a post and core, and a tapered threaded end having tapered, self-tapping threads. The cavity is configured to have flat walls forming a hexagonal or other polygonal interior surface. This interior surface also has screw threads superimposed on the polygonal surface. The anchor is thus of reduced axial length than prior art anchors having threads and polygonal surfaces not superimposed. The tapered threads formed on the tapered threaded end engage different areas of bone tissue. Since bone tissue may not be homogeneously strong and resilient, this arrangement helps assure that some threads will engage strong, resilient bone tissue. This threading preferably comprises buttress type threads. A pitched relief groove extends across all convolutions of the external, self-tapping threads formed on the tapered end. These self-tapping threads are buttress threads. The pitch of the relief groove is angled to vary from that of the threads, so that the groove intersects all threads, but the pitch is inclined in the same direction as that of the threads. The groove thus complements screwing action of the self-tapping threads.

4 Claims, 3 Drawing Sheets 5,601,429

DENTAL IMPLANT ANCHOR

BACKGROUND OF THE INVENTION

1. Field of the Invention

The present invention relates to an anchor which is inserted into a bone for the purpose of receiving a post and core. The anchor threads to bone tissue, and provides structure for secure mounting of the post and core within the mouth.

2. Description of the Prior Art

Replacement or artificial teeth have become available as an answer to the loss of original teeth. Natural or original teeth are secured in place by roots, which cooperate with the body tissue. When a natural or original tooth is lost, the root is usually also lost. Secure attachment for the new tooth must be provided which will hold and support the tooth securely enough to resist forces generated in biting and chewing.

In contemporary practice, a socket or receptacle for receiving the tooth is placed in the jaw bone, and a post and core assembly is set into the receptacle. The receptacle must cooperate with the natural body into which the new tooth is set. Usually, underlying bone tissue is drilled to accept an anchor. The anchor is threaded into the bone, the anchor frequently serving as its own tap to form threads in the bone.

The receptacle normally secures the post and core or healing screw in one of two ways. For temporary, removable securement, the healing screw is threaded into the receptacle. For permanent securement, the hexagonal shank of the post engages a cooperating bore formed in the anchor, and the engagement is cemented into place.

Normally, the anchor is provided with self-tapping threads, and engages the bone by being screwed into a hole bored into the bone. The self-tapping threads carve cooperating threads into the unthreaded hole in the bone. In all known prior art threading schemes, the final diameter of the threads formed in the bone is achieved by the first convolutions of the self-tapping threads of the anchor.

U.S. Pat. No. 4,863,383, issued to Hans L. Grafelmann on Sep. 5, 1989, illustrates an implant having an anchor which has a tapered body. Unlike the present invention, the screw threads are of constant outer diameter throughout the length of the anchor. This is in contrast to the present invention, wherein threads are of progressively increasing outer diameter.

Grafelmann also provides the upper end of his anchor with an opening for receiving a post, which opening has both a hexagonal portion and also female threading. The threading is located below the hexagonal portion. By contrast, the present invention locates both a hexagonally walled opening and female threading at the same level along the length of the anchor, in a superimposed manner.

U.S. Pat. No. 5,078,607, issued to Gerald A. Niznick on Jan. 7, 1992, U.S. Pat. No. 5,246,369, issued to Francis Poulmaire on Sep. 21, 1993, and U.S. Pat. No. 5,312,256, issued to Gerard Scortecci on May 17, 1994, further illustrate anchored dental implants. In all cases, external threading engaging bone tissue is of constant diameter, unlike that of the present invention. Also unlike the present invention, these inventions lack female threading superimposed on a hexagonally walled cavity, for receiving a post of a subsequently installed component.

None of the above inventions and patents, taken either singly or in combination, is seen to describe the instant invention as claimed.

SUMMARY OF THE INVENTION

The present invention improves over prior art implants in both tapping bone tissue in a more effective manner, and in reducing overall length of the anchor by superimposing internal threading over a hexagonally walled cavity. The former characteristic is achieved by providing self-tapping male threads of progressively increasing external diameter, by providing a vent or relief groove pitched in the same direction as the threads, and by employing buttress threads.

These buttress threads are formed on a tapered body. The tapered configuration of the body, and hence the threads, assures that the threads will engage bone tissue at various points. This increases chances of engaging a strong and resilient portion of the bone tissue. It is possible that bone tissue, which is not homogeneous, would provide inadequate support and engagement in localized weak or poor areas.

Cutting action of tapping is improved by relief grooves extending longitudinally through all convolutions of the self-tapping threads. The relief grooves are inclined in the same direction as that of the pitch of the threads, so that the groove complements engagement by the threads.

The invention also enables a more compact anchor, considered with respect to overall length in the axial dimension. Since the mounting posts of some tooth and core assemblies require both temporary and removable installation and also permanent installation, posts have threads and polygonal shanks. The usual arrangement is that the threads are located serially with respect to the polygonal shank. In cavity of the present invention, the threads are superimposed on the polygonal wall. This portion of the overall length thus serves two purposes, and axial length is thus limited.

External threads for engaging bone tissue are preferably buttress threads. This arrangement opposes unintended withdrawal of the anchor from bone tissue.

Accordingly, it is a principal object of the invention to provide a dental implant anchor which accepts both threaded and hexagonal shanks along the same axial extent.

It is another object of the invention to provide a dental implant anchor which is compact in its overall length.

It is a further object of the invention to cause external threads to engage different areas of bone tissue.

Still another object of the invention is that a relief groove extend longitudinally through all convolutions of self-tapping threads.

An additional object of the invention is that the relief groove complement engagement action of the external threads as the anchor is threaded into bone tissue.

It is again an object of the invention to oppose unintended withdrawal of the anchor from bone tissue.

It is an object of the invention to provide improved features and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
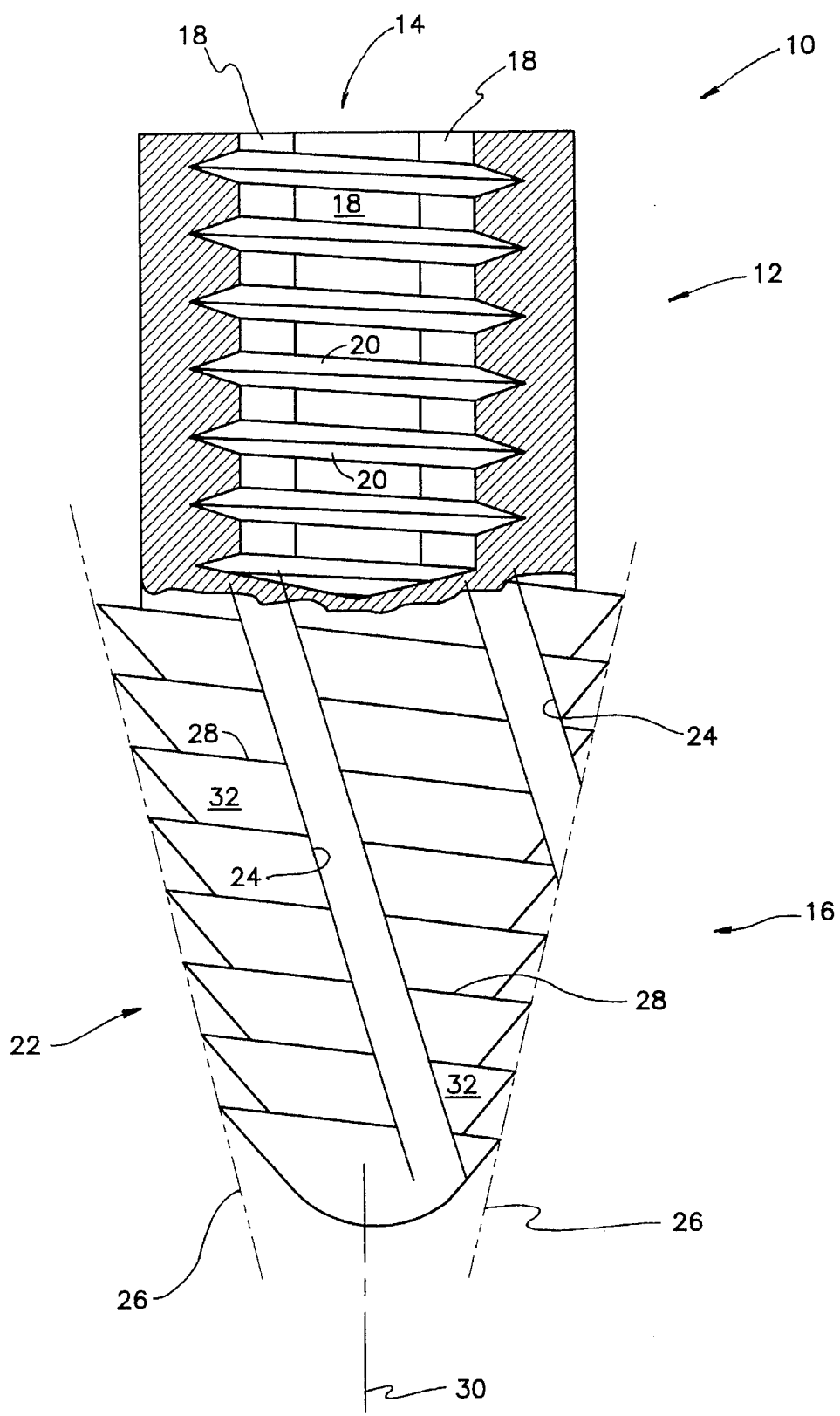
FIG. 1 is a side elevational, partially cross sectional view of the invention.
Figure 2:
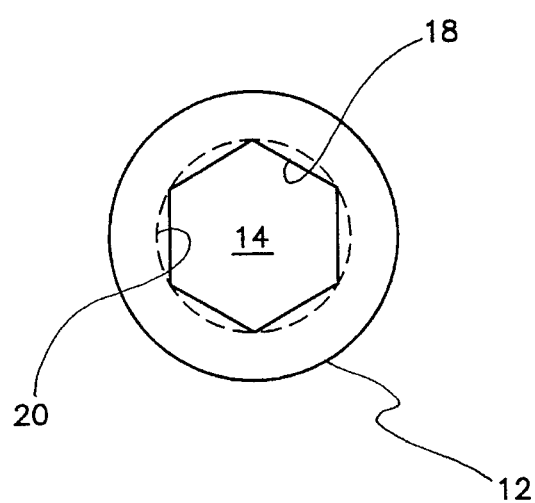
FIG. 2 is a top plan detail view of the upper section of the invention.

Turning now to FIG. 1 of the drawings, the novel dental implant anchor 10 is seen to comprise an elongated body including an upper section 12 having an internal cavity 14 open at the top located at a proximal end of the body, and a lower, tapered section 16. Cavity 14 is polygonal in cross section, as seen in FIG. 2. Cavity 14 has flat facets 18 which, as depicted, form a hexagon. However, any polygon may be defined by facets 18.

A female thread 20 is formed in the flat facets 18 of the interior walls of cavity 14. Threads 20 are superimposed over facets 18, so that a post (not shown) of a post and core (not shown) may be screwed thereinto. The post and core assembly is a second component of an artificial replacement tooth secured or mounted within a person's jaw by anchor 10. The post is screwed into cavity 14 for temporary, removable mounting, and later slid and cemented into place for permanent mounting.

This arrangement allows cavity 14 to both thread to a post, and to slidingly accept a post of the second component, while remaining axially more compact than would be the case if threads 20 and facets 18 were arranged in stacked or series relationship.

External threads 22 are located on lower section 16 of anchor 10. A relief groove 24 is formed in threads 22, extending through all convolutions of threads 22. Grooves 24 cause threads 22 to be the self-tapping type, incising appropriate corresponding female threading into bone tissue.

Section 16 of anchor 10 is seen to taper to a small diameter at the distal end, that being the lower end as shown in FIG. 1. The crests of each thread collectively define a tapered outermost boundary, this boundary being indicated by imaginary lines 26. Individual convolutions of threads 22 thus contact bone tissue at different sections of bone tissue (not shown). These different sections of bone tissues are not in overlying relationship to one another when tapered threading is employed. This arrangement accommodates the possibility that strength and resilience of bone tissue may vary throughout the jaw by increasing the likelihood that at least one convolution will engage a strong area of the bone tissue.

Upper section 12 is seen to be of less diameter than the largest diameter of threads 22.

It is preferred that threads 22 be buttress type threads, in which the top surface 28 of each convolution of threading is horizontal. In this sense, the term "horizontal" signifies that surface 28 does not incline with increasing distance from the longitudinal axis 30 of anchor 10, and is not visible in side elevation.

It will be seen that corresponding lower surfaces 32 of each convolution of threading are tapered, having a smaller diameter at the lower end of each convolution than that of the upper end of each convolution. The angle of the lower surfaces 32 acts as a guide, in the sense of a funnel or shoehorn, promoting downward movement of anchor 10 into the cavity (not shown) drilled into the bone tissue. The lack of a corresponding inclination of upper surfaces 28 opposes upward movement of anchor 10 after installation into bone tissue. This feature promotes secure and permanent setting of anchor 10 in the bone tissue.

Threads 22 have a pitch which, in the depiction of Fig. 1, causes the top surface 28 of each convolution to be inclined such that the left side is higher than the right side. Each groove 24 also has a pitch, which also has an inclination. Grooves 24 are preferably spiralled around section 16 of anchor 10, extending longitudinally along anchor 10. The pitch of grooves 24 and that of threads 22 are inclined in the same direction, although at differing angles with respect to a vertical direction. The effect of grooves 24 is thus complementary to the effect of threads 22 when threading anchor 10 into bone tissue.

Figure 3:
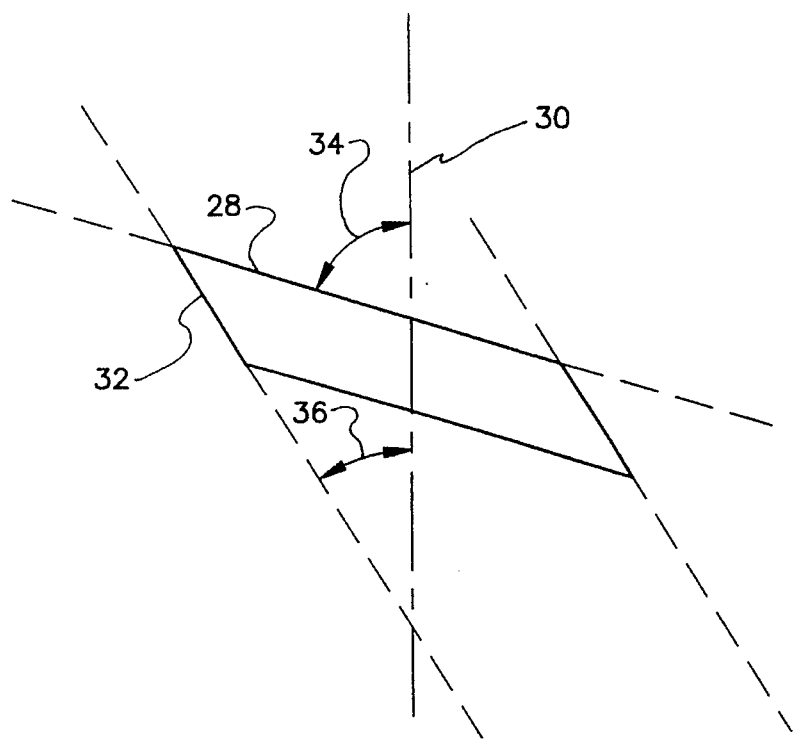
FIG. 3 is a detail diagrammatic representation of external threading shown at the lower half of FIG. 1, depicting critical angular relationships between threads and the longitudinal axis of the novel dental implant anchor.

As shown in FIG. 3, upper surfaces 28 of each convolution of threads 22 are oriented at a relatively great angle 34 to the vertical direction (indicated by longitudinal axis 30), compared to the corresponding angle 36 formed by lower surfaces 32.

Figure 4:
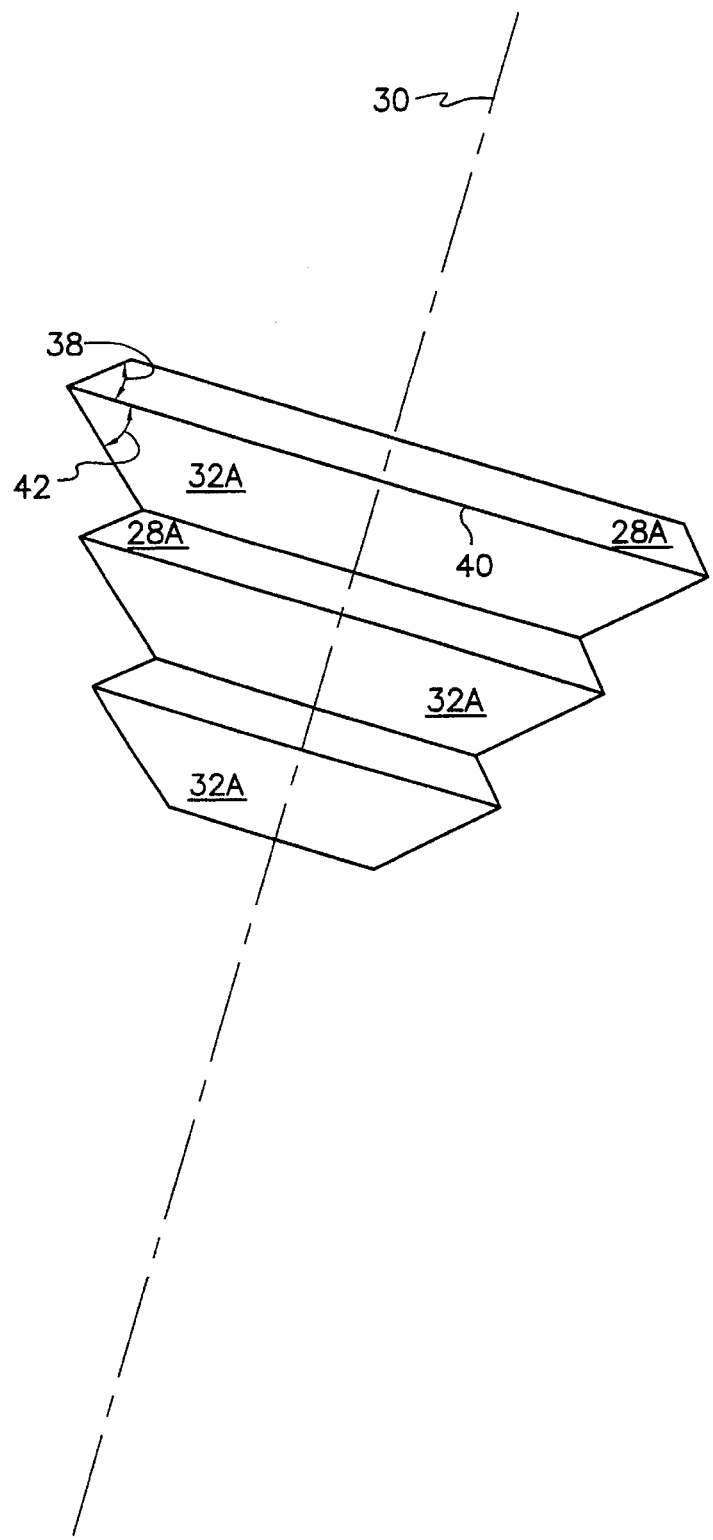
FIG. 4 is a side elevational detail view of an alternative embodiment of threading shown at the lower half of FIG. 1.

While buttress threads are the preferred form of threads 22, it may be easier to fabricate anchor 10 in an alternative embodiment shown in FIG. 4. In this embodiment, the top surface 28 of each convolution of threads 22 incline downwardly with increasing radial distance from axis 30.

Inclination or slope of upper and lower surfaces 28A and 32A is different in two aspects. One aspect is that as previously mentioned, surfaces 28A incline downwardly from axis 30. This signifies that those points on surfaces 28A located at greater distance from axis 30 are closer to the bottom of this drawing figure than are points located relatively close to axis 30. By contrast, surfaces 32A incline upwardly from axis 30. This signifies that points located on surfaces 32A located at greater distance from axis 30 are closer to the top of this drawing figure than are points on surfaces 32A located at relatively close proximity to axis 30. Thus, pitch of surfaces 32A is inverted, compared to that of surfaces 28A.

Inverted inclination is only one aspect in which surfaces 28A and 32A differ. The second aspect is that the absolute value of the respective included angles relative to the pitch line of the threads differ in magnitude. Referring to surfaces 28A, there exists a first included angle 38 defined between thread pitch line 40 and the upper surface 28A. Referring now to surfaces 32A, a second included angle 42 exists between thread pitch line 40 and lower surface 32A. Angle 38 is an acute angle greater than zero and angle 42 is an acute angle of magnitude greater than that of angle 38. The threads of FIG. 4 may be termed modified buttress threads.

Obviously, certain variations and modifications may be introduced by those of skill in the art without departing from the inventive concept. For example, threading 20 and 22 may be either right handed or left handed. In either case, grooves 24 will be like handed with respect to threading 22, although of different pitch. In a further example, individual facets 18 (see FIG. 2) of cavity 14 may be unequal in length to one another.

It is to be understood that the present invention is not limited to the embodiments described above, but encompasses any and all embodiments within the scope of the following claims.

I claim:

1. A dental implant anchor for receiving and securing a replacement tooth within a person's jaw, said anchor having an elongated body including a proximal end and a distal end, said proximal end having means defining a cavity for receiving a post of a post and core component of the replacement tooth secured within said anchor, said body being tapered at said distal end, and having external threads having crests collectively defining a tapered outermost boundary and a thread pitch line, whereby said external threads engage different sections of bone tissue, said external threads having an upper surface defining a first angle included between said upper surface and said thread pitch line, and a lower surface defining a second angle included between said lower surface and said thread pitch line, said first angle being an acute angle greater than zero and said second angle being an acute angle greater in magnitude than that of said first angle, whereby unintended withdrawal from bone tissue is opposed by said external threads, said body further comprising means defining a plurality of spiralled relief grooves extending longitudinally along said body and extending through all convolutions of said external threads, said external threads having a first pitch, and said spiralled relief groove having a second a pitch of magnitude different from that of said first pitch, said second pitch oriented in the same direction as said first pitch of said external threads, whereby said spiralled relief groove acts in a complementary manner with respect to said external threads.

2. The dental implant anchor according to claim 1, said cavity having flat facets defining a polygonal internal surface, and female threads superimposed on said flat facets of said polygonal internal surface, whereby said cavity is compact, while accepting both polygonal and threaded posts of a replacement tooth.

3. The dental implant anchor according to claim 1, said proximal end of said body having a diameter less than the maximal diameter of said external threads of said distal end of said body.

4. A dental implant anchor for receiving and securing a replacement tooth within a person's jaw, said anchor having an elongated body including a proximal end and a distal end, said proximal end having means defining a cavity for receiving a post of a post and core component of the replacement tooth secured within said anchor, said cavity having flat facets defining a polygonal internal surface, and female threads superimposed on said flat facets of said polygonal internal surface, whereby said cavity is compact, while accepting both polygonal and threaded posts of a replacement tooth;

said body being tapered at said distal end, and having external modified buttress threads having crests collectively defining a tapered outermost boundary, said external threads having an upper surface oriented at a first angle with respect to a vertical direction, and a lower surface oriented at a second angle with respect to the vertical direction, whereby said external threads engage different sections of bone tissue, said external threads having an upper surface defining a first angle included between said upper surface and said thread pitch line, and a lower surface defining a second angle included between said lower surface and said thread pitch line, said first angle being an acute angle greater than zero and said second angle being an acute angle greater in magnitude than that of said first angle, whereby unintended withdrawal from bone tissue is opposed by said external threads, said proximal end of said body having a diameter less than the maximal diameter of said external threads of said distal end of said body;

said body further comprising means defining a plurality of spiralled relief grooves extending longitudinally along said body and extending through all convolutions of said external threads, said external threads having a first pitch, and said spiralled relief groove having a second and pitch of magnitude different from that of said first pitch, said second pitch oriented in the same direction as said first pitch of said external threads, whereby said spiralled relief groove acts in a complementary manner with respect to said external threads.

\* \* \* \* \*